(12) United States Patent
Schaffner et al.

(10) Patent No.: US 10,799,357 B2
(45) Date of Patent: Oct. 13, 2020

(54) MEDICAL INSTRUMENT AND METHOD FOR HEART VALVE REPAIR

(71) Applicant: CoreMedic AG, Biel (CH)

(72) Inventors: Silvio Schaffner, Berlingen (CH); Tobias Aeschlimann, Burgdorf (CH); Oliver Wüthrich, Herrenschwanden (CH); Thomas Bauer, Allensbach (DE)

(73) Assignee: COREMEDIC AG, Biel (CH)

( * ) Notice: Subject to any disclaimer, the term of this patent is extended or adjusted under 35 U.S.C. 154(b) by 274 days.

(21) Appl. No.: 15/768,887

(22) PCT Filed: Oct. 19, 2016

(86) PCT No.: PCT/CH2016/000138
§ 371 (c)(1),
(2) Date: Apr. 17, 2018

(87) PCT Pub. No.: WO2017/066890
PCT Pub. Date: Apr. 27, 2017

(65) Prior Publication Data
US 2018/0303614 A1 Oct. 25, 2018

(30) Foreign Application Priority Data
Oct. 21, 2015 (CH) ...................................... 1535/15

(51) Int. Cl.
*A61F 2/24* (2006.01)
*A61B 17/04* (2006.01)
(Continued)

(52) U.S. Cl.
CPC ...... *A61F 2/2457* (2013.01); *A61B 17/00234* (2013.01); *A61B 17/0401* (2013.01);
(Continued)

(58) Field of Classification Search
CPC .......... A61B 17/00234; A61B 17/0401; A61B 17/0482; A61B 2017/00243;
(Continued)

(56) References Cited

U.S. PATENT DOCUMENTS

2007/0004995 A1 3/2007 Weiss
2007/0118151 A1 5/2007 Davidson
(Continued)

FOREIGN PATENT DOCUMENTS

AU 2014 234 126 10/2015
WO 2012/040865 4/2012

OTHER PUBLICATIONS

International Preliminary Report on Patentability dated Apr. 24, 2018 (Apr. 24, 2018), Application No. PCT/CH2016/000138, 9 pages.

*Primary Examiner* — Shaun L David
*Assistant Examiner* — Mohamed G Gabr
(74) *Attorney, Agent, or Firm* — Rankin, Hill & Clark LLP

(57) ABSTRACT

A surgical instrument implementing a leaflet grabbing mechanism by a leaflet grabbing structure, in which the leaflet can be grabbed and clamped between first and second abutment surfaces. The first, proximally facing abutment surface belongs to a swivel-out portion of the leaflet grabbing structure, which includes at least a first arm and a second arm. In a released state, when the leaflet grabbing structure is released from a catheter, the arms are capable of swiveling: the first arm may swivel with respect to a main body to which it is attached, and the second arm may swivel relative to the first arm so that in a leaflet grabbing position the first abutment surface faces proximally. The second arm includes a recess arranged so that a chord extending between a released distal implant part and a proximal implant part can
(Continued)

extend therethrough and be released by a lateral relative movement.

16 Claims, 4 Drawing Sheets

(51) Int. Cl.
  *A61B 17/00* (2006.01)
  *A61B 90/00* (2016.01)
(52) U.S. Cl.
  CPC ........ *A61F 2/2466* (2013.01); *A61B 17/0482* (2013.01); *A61B 2017/00243* (2013.01); *A61B 2017/00336* (2013.01); *A61B 2017/0409* (2013.01); *A61B 2017/0417* (2013.01); *A61B 2017/0437* (2013.01); *A61B 2017/0458* (2013.01); *A61B 2017/0464* (2013.01); *A61B 2090/036* (2016.02); *A61B 2090/0807* (2016.02)

(58) Field of Classification Search
  CPC .. A61B 2017/00336; A61B 2017/0409; A61B 2017/0417; A61B 2017/0437; A61B 2017/0458; A61B 2017/0464; A61B 2090/036; A61B 2090/0807; A61F 2/2457; A61F 2/2466
  See application file for complete search history.

(56) References Cited

U.S. PATENT DOCUMENTS

| | | |
|---|---|---|
| 2011/0011917 A1 | 1/2011 | Loulmet |
| 2015/0032127 A1 | 1/2015 | Gammie et al. |
| 2016/0045315 A1* | 2/2016 | Vola .................. A61B 17/0469 623/2.11 |

* cited by examiner

MEDICAL INSTRUMENT AND METHOD FOR HEART VALVE REPAIR

BACKGROUND OF THE INVENTION

Field of the Invention

The invention is in the field of minimally invasive surgical and interventional cardiology devices for heart valve repair. It particularly relates to an instrument for repairing an atrioventricular heart valve, in particular the mitral heart valve or also the tricuspid heart valve in a minimally invasive manner, and to an according method.

Description of Related Art

Prolapses of a leaflet of the mitral valve into the left atrium and resulting valve insufficiency can cause serious dysfunctions of the heart. One reason for such prolapse are damaged tendons (chordae tendineae) that connect the leaflets of the mitral valve to the papillary muscle through the left ventricle. Such damage may, for example, be a result of a myocardial infarction, tissue degeneration or infectious disease.

A repair of such a prolapse demands the leaflet or leaflets to be re-connected to the papillary muscle, for example by synthetic fibres, such as Gore-Tex® fibres. Such an approach in accordance with the state of the art demands suturing the implant to a papillary muscle. A first disadvantage of such a repair process is that it is only possible while the heart is inactive, thus the surgical repair demands that the heart is stopped and drained of blood, while a cardiopulmonary bypass is used. A second disadvantage is that the success of the operation depends strongly on the skill of the surgeon. A further disadvantage is that the fibres sutured to the leaflet may cause long-time damage.

In WO 2012/040865, approaches are presented according to which a distal anchor attached to a filament serving as artificial chord is used that can be shot across the left ventricle. Also tools for fixing an artificial chord to the leaflet and tools for temporary fixation of the leaflet of the beating heart are illustrated.

US 2011/0011917 describes methods and devices for cardiac valve repair. The devices may include a dart anchor with self-expandable legs for being secured into cardiac tissue and a staple to be deployed into tissue of the leaflet, which staple may be secured to a tensile member that is also connected to the dart anchor. A pledget may be used to spread loads, i.e. to prevent the leaflet tissue from being injured by the staple. US 2011/0011917 also discloses an anchor with an eyelet in which a chord can slide. This anchor is to be attached to a leaflet.

These prior art methods that are based on sutures feature the disadvantage that suturing in minimally invasive setups is difficult, and therefore sufficiently reliable stability is often difficult to achieve.

SUMMARY OF THE INVENTION

It is an object of the present invention to provide an instrument for repairing an atrioventricular heart valve, in particular the mitral heart valve or also the tricuspid heart valve, and an according method, which instrument and method overcome drawbacks of prior art devices and methods and which ensure easy implantation, are suited also for interventional surgery and provide a reliable and well tissue-compliant repair. Especially, if the surgical operation is carried out in a minimally invasive manner on the beating heart, the leaflet has to be held still for the operation, and the instrument and method should in embodiments provide solutions for this.

In accordance with an aspect of the invention, a surgical instrument implementing a leaflet grabbing mechanism by a leaflet grabbing structure is provided. More in particular, the leaflet grabbing mechanism includes a first, proximally facing abutment surface and a second, distally facing abutment surface, wherein the abutment surfaces are movable with respect to one another so that the leaflet can be grabbed and clamped between the first and second abutment surfaces. The first, proximally facing abutment surface belongs to a swivel-out portion of the leaflet grabbing structure. More in particular, swivel-out portion includes at least a first arm and a second arm. In a non-released state, when the leaflet grabbing structure is contained in an outer tube, the first and second arms are in a folded position relative to one another. In a released state, when the leaflet grabbing structure is released from the outer, first tube ("catheter"), the arms are capable of swiveling: the first arm is capable of swiveling out with respect to a main body to which it is attached, and the second arm is capable of swiveling relative to the first arm so that in a leaflet grabbing position the first abutment surface faces proximally. Especially, the first abutment surface is a surface of the second arm. The second arm may be secured directly to the first arm in a swiveling manner, or the second arm may be secured to a further element (intermediate element) that is directly or indirectly secured to the first arm.

The second arm may, in the leaflet grabbing position, especially be oriented such that the first abutment surface is essentially perpendicular to the axial direction.

The second arm includes a recess arranged so that a chord, for example, extending between a released distal implant part (that will be released distally of the second arm while the leaflet is being grabbed) and a proximal implant part (that will be released proximally of the leaflet, thus proximally of the second arm while the leaflet is being grabbed) can extend therethrough and be released by a lateral (radial) relative movement. To this end, the recess is open to a side ("side" or "lateral" in this text unless otherwise specified are used to denote directions that are radial with respect to the axis) and extends to the intersection of the first abutment surface with the axis. The first abutment surface may be constituted by a region around the innermost portion of the recess of the proximally facing surface of the second arm.

The outer tube or another tube of the instrument may be a steerable catheter. Steerable or deflectable catheters are known in the art of minimally invasive surgery. It would also be possible to make an interior tube steerable.

The second abutment surface may be constituted by a press pad formed by a distal end face of the counterportion that is releasable from the tube and axially movable relative to the main body. The counterportion or at least a distal end part thereof may for example be essentially tube shaped or have the shape of a slitted tube to release the proximal implant part from it while the leaflet is being clamped.

The press pad formed by the counterportion may have a circular outer contour or may also be angular (such as rectangular or pentagonal or hexagonal etc.).

The press pad may, especially at its distal end, be provided with a cushion to prevent the tissue from becoming damaged.

The dimensions of the recess and of the counterportion are adapted to each other so that the distal end face of the counterportion and the second arm's proximally facing surface (in the leaflet grabbing position) have a substantial overlap while an axial continuation of the lumen within the counterportion coincides with the innermost portion of the recess so that a needle released from inside the counterportion while the same is pressed against the second arm is not impeded. More in particular, an axial position of an inner surface of the counterportion may approximately follow the inner contour of the recess along its innermost portion.

More in particular, the instrument may in embodiments include a needle arranged in an interior of the counterportion and being movable with respect to the counterportion in axial directions to be released from the interior of the counterportion to pierce the leaflet when it is clamped between the first and second abutment surfaces. The needle may be cannulated to form a needle tube ("inner tube" in this text). Within the needle, the chord and for example parts of an implant may be arranged. The chord may be pre-mounted to the implant parts, with a fixed or adjustable length. An adjustable length may for example be possible by a slidable knot. Alternatively, the chord may have to be mounted to the implant parts or one of the implant parts in a separate method step.

A handle by which the surgeon operates the needle tube may include a depth indicator to control the distance by which the needle has been deployed. In addition or as an alternative, the needle may include at least one marking that indicates the penetration depth and that may be supervised by imaging methods.

Due to the described approach, the instrument may be an all passive construction making implantation on the beating heart possible without any active power source except the pulling and pushing of wires and steering of the steerable catheter by the surgeon. Especially, it is not necessary that parts, such as an implant part, are actively shot out or similar. This makes possible a good control of the operation by the surgeon.

In embodiments, the device includes the implant parts in a pre-assembled or pre-assemblable configuration. Especially, the implant parts may include a distal implant part to be anchored in tissue, such as muscle tissue, and a proximal implant part to be secured to the leaflet and for example to be arranged proximally of the leaflet, with the chord extending through a perforation of the leaflet to the distal implant part.

In embodiments, the proximal implant part in contrast to prior art approaches may be configured to lie flat on a surface of the leaflet tissue, with the chord extending from the proximal implant part through the leaflet tissue and through the ventricle to the distal implant part. To this end, the proximal implant part may, for example, include a flattish distally-facing abutment surface (distally-facing in the implanted state, i.e. facing to the side to which the chord runs). This is in contrast to prior art approaches that teach to clamp the leaflet by a leaflet anchor or to other prior art approaches that teach to suture the leaflet.

Especially, the proximal implant part may be configured to only lie on the leaflet and to thereby being secured to it—without the proximal implant part having any fastening mechanism that extends within the leaflet or through the leaflet.

The proximal implant part may hold to the leaflet without any additional fastening mechanism (such as a suture) or artificial fastening means, only by the design of the implant as such that includes the distally facing abutment surface lying on the leaflet tissue—especially by the chord extending through the leaflet tissue and the ventricle to the distal implant part, possibly assisted by a distally-facing structure on the abutment surface that includes portions that protrude into the tissue, without penetrating through it, and/or is indented with respect to it, to prevent shifting movements.

The proximal implant part especially will, after implantation, be placed on one side of the leaflet only and not, for example, extend through the leaflet. The side on which the proximal implant part lies on the leaflet tissue is the atrium-facing upper side of the leaflet.

Especially, the proximal implant part is free of any clamping mechanism and does not include any portion that bears against the ventricle-facing lower surface of the leaflet.

As such, the proximal implant part is capable of coupling distally facing forces (forces towards the side of the ventricle) into the leaflet but its structure would not allow to couple proximally-facing forces into the leaflet (the proximal implant part cannot pull the leaflet towards the atrium side) and vice versa.

In embodiments, at least the proximal implant part and for example both/all implant parts may be carried by an anchor carrier inside the inner tube.

Especially, the proximal implant part may be assembled with the anchor carrier in a manner that it can escape and is released automatically as soon as the proximal implant part and the portion of the anchor carrier to which it is mounted is outside of the tubular element—for example without any active mechanism that causes the release, thus just by being moved out of the tubular element.

For example, the anchor carrier may axially extend within the tubular element from proximally of the proximal implant part to at least a center of the proximal implant part and for example at least to its distal end or further than its distal end. Especially, the anchor carrier may extend over the full (proximodistal) length of the proximal implant part.

In embodiments, the anchor carrier may form a seat for the proximal implant part, out of which the proximal implant part can escape by being moved in radial direction once it is released from the tubular element, i.e. the seat is open towards one radial direction but blocks the second implant part with respect to axial directions as long as it is kept in the seat by the tubular element.

The seat for this purpose may have a structure adapted to the shape of the proximal implant part in the initial (not spread) state. Especially, the anchor carrier may have a distal foot portion with a channel for the chord, and, proximally thereof, a seat portion (also referred to as shaft portion in this text) in which the cross section is reduced to accommodate the proximal implant part. Proximally of the seat portion, the anchor carrier may have a pusher portion that has a larger cross section than the seat portion so that a pushing movement of the anchor carrier also pushes the second implant part forward as long as the second implant part is still located in the seat and not yet released.

In case the anchor carrier also carries the distal implant part in addition to the proximal implant part, it may be such that the implant parts are arranged beside one another, with the proximal implant part arranged proximally of the distal implant part. The inner tube or a sleeve element inside the inner tube may prevent the proximal implant part from escaping from the anchor carrier as long as the anchor carrier is within the inner sleeve or tube element.

The counterportion may be straight with respect to the axis and be movable in a straight axial direction.

In the folded position, the first and second arms (including any intermediate part if present) fit into the outer tube. Especially, in the folded position, the first arm may extend axially distally of the main body, and the second arm may be secured to the distal end of the first arm and be folded back to lie parallel with the first arm.

Configurations in which the second arm in the folded position extends further distally from the location at which it is secured to the first arm—thus stretched configurations are possible also.

In the swiveled-out position, the first arm may extend distally from the main body, at an acute angle to the axis, and the second arm is folded away from the first arm, especially to be approximately perpendicular to the axis.

For bringing the leaflet grabbing structure from the folded position to the swiveled-out position, the instrument may include a cable pull mechanism. Such a mechanism may for example include a wire appropriately guided along the main body and the first arm to the second arm, with which it is appropriately connected to pull it out into the swiveled-out position.

One or more springs may act to bring the leaflet grabbing structure back into the folded position as soon as the cable pull mechanism is not active any more.

Of course, other variants are possible. This includes the possibility that one or more springs automatically bring the leaflet grabbing structure into the swiveled-out position (unfolded position), and an active mechanism, such as a cable pull mechanism, is provided to bring it back into the folded position. It is also possible that the leaflet grabbing structure automatically assumes—for example by one or more springs—the swiveled-out position as soon as it is released from the outer tube (catheter) and is brought back into the folded position by being retracted into the outer tube. Such a variant is especially easy to implement if the folded position is a stretched configuration. In a further variant, both for bringing the leaflet grabbing structure into the swiveled-out position and for bringing it back into the folded position, an active mechanism, such as a cable pull mechanism or similar may be provided.

In embodiments, the device includes a feedback indicator showing whether or not the leaflet grabbing structure has grabbed the leaflet. Such indicator may for example include an optical means such as a light guide defining a light path to the distal end back, which light path is interrupted when the leaflet has been grabbed.

The invention also concerns a method of replacing or supplementing damaged natural chordae tendineae of a human or animal heart by using a device as described in this text. Features that were described in this text referring to the instrument may also belong to the method, and vice versa.

Especially, the method may include the steps of:
providing an instrument, the instrument including:
  A first tube having a tube axis defining an axial direction;
  Arranged within the first tube, a leaflet grabbing structure, the leaflet grabbing structure including a main body, a swivel-out portion with a first arm mounted to the main body, and a second arm, the second arm being swivel-mounted relative to the first arm, the first arm being swivel-mounted with respect to the main body;
  Wherein the second arm includes, in a swiveled-out position of the first and second arms, a proximally facing abutment surface;
  The leaflet grabbing structure further including a counterportion releasable from the tube and being movable relative to the main body in axial directions, the counterportion including a distally-facing second abutment surface that is pressable, by a force pointing towards a distal direction, against the first abutment surface;
  And wherein the second arm has a recess and extends to a position that is central with respect to the tube axis;
advancing the tube from an atrial side towards a leaflet of an atrioventricular valve of the heart,
clamping the leaflet between the first and second abutment surfaces;
securing an artificial chord to the clamped leaflet; and
removing the leaflet grabbing structure.

For the step of securing the artificial chord, a method with the following steps may be used:
providing a system, the system including:
  a tubular element having an outer, distal end,
  a distal implant part arranged in the tubular element,
  the chord, being an artificial or allograft or xenograft chord arranged in the tubular element,
  a proximal implant part arranged in the tubular element, and
  an anchor carrier arranged in the tubular element,
  the distal implant part and the proximal implant part being arranged in the tubular element beside one another,
  the proximal implant part being assembled with the anchor carrier inside the tubular element so that the tubular element prevents the proximal implant part from escaping from the anchor carrier as long as the anchor carrier is within the tubular element,
advancing the tubular element from an atrial side to a leaflet of an atrioventricular valve of the heart, piercing the leaflet and advancing the tubular element through the pierced leaflet and through the ventricle towards tissue;
releasing the distal implant part from the tubular element and thereby implanting it in the tissue;
retracting the tubular element and releasing the proximal implant part proximally of the leaflet, on the atrial side thereof; and
removing the tubular element,
wherein either the proximal implant part and the distal implant part are connected by the chord in the system, or the method includes the additional step of connecting the proximal and distal implant parts by the chord.

In this, the tubular element may be arranged within the tube, for example within the part that includes the counterportion. Especially, the tubular element may have a distal end constituting a needle deployed from the counterportion while the leaflet is clamped or be present within such needle.

BRIEF DESCRIPTION OF THE DRAWINGS

Hereinafter, principles and embodiments of the invention are described referring to drawings. Same reference numbers in the drawings refer to same or analogous elements. The drawings show.

DESCRIPTION OF THE PREFERRED EMBODIMENTS

Figure 1:
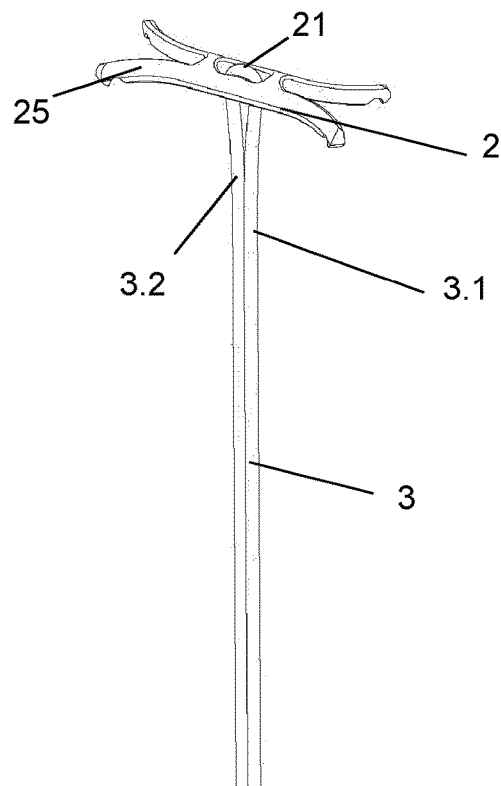
FIG. 1 an implant having a proximal implant part and a distal implant part, coupled by a chord.

The implant illustrated in FIG. 1 includes a distal implant part 1, a proximal implant part 2 and a chord 3 connecting the proximal and distal implant parts. The chord is guided from a distal end of the distal implant part to the proximal implant part and through the proximal implant part back to the distal end of the distal implant part, so that the chord 3 is doubled and has two chord portions 3.1, 3.2 between the proximal and distal implant parts. Within the distal implant part and between the distal and proximal ends thereof, the chord portions 3.1, 3.2 are guided in a shaft 13, and they are secured by a knot 5 distally of the distal implant part.

In alternative embodiments, instead of a knot, other techniques could be used for securing the distal implant part to the chord, for example crimping, welding, etc.

The distal implant part 1 includes the shaft 13 having a longitudinal through opening for the chord and a plurality of legs 15 protruding backwardly and being bent radially outwardly.

Figure 2:
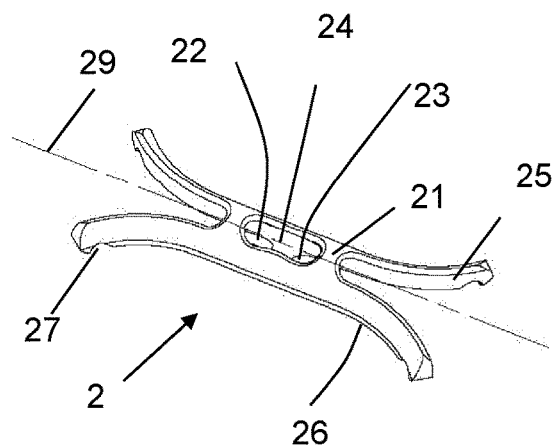
FIG. 2 the proximal implant part.

The proximal implant part 2 is shown in somewhat more detail in FIG. 2. The proximal implant part is elongate defining a longitudinal axis 29. It has a central body 21 and four arms 25 one-piece with the central body and extending outwardly from the central body.

The lower side of the central body and the arms forms an abutment surface that after implantation rests against the leaflet tissue after implantation.

The chord 3 mechanically couples the proximal implant part 2 and the distal anchor part 1 with each other and defines a maximum distance between these implant parts. To this end, the proximal implant part has a first chord opening 22 and a second chord opening 23 separated by a bridge 24. The chord runs through the first chord opening, over the bridge and back to the second chord opening so that it is looped through the proximal implant part. The bridge 24 has rounded features so that the chord can slide along it easily without being damaged. The first and second openings are positioned so that the center of the abutment area is in the middle between them.

Because the openings are centrally located in the proximal implant part, a pulling force coupled into the chord acting on the proximal implant part will not cause any torque on the proximal implant part.

While in the depicted configuration the chord 3 is doubled and looped through the proximal implant part, this effect could for example also be achieved if the chord was one-way only and attached to a spot of the center of area or runs through a single opening in the center of area.

The arms 25 of the proximal implant part 2 are bent outwardly away from the axis. Thereby, the proximal implant part is better supported by the leaflet tissue. On the abutment surface, the arms each include an optional hook feature 27.

Figure 3:
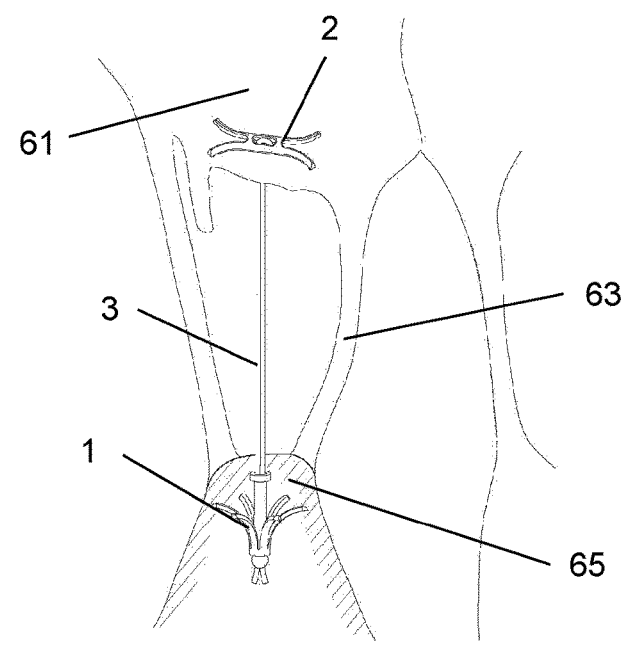
FIG. 3 the implant implanted in a human heart.

FIG. 3 shows the distal implant part 1 anchored in the papillary muscle. The artificial chord 3 runs through the ventricle and through an opening of the leaflet; the proximal implant part is placed on the proximal side of the leaflet 61, with the abutment surface resting on the leaflet tissue. By this, the implant assists the natural chordae 63 if they are damaged or otherwise not sufficient for the mitral valve to close sufficiently.

Figure 4:
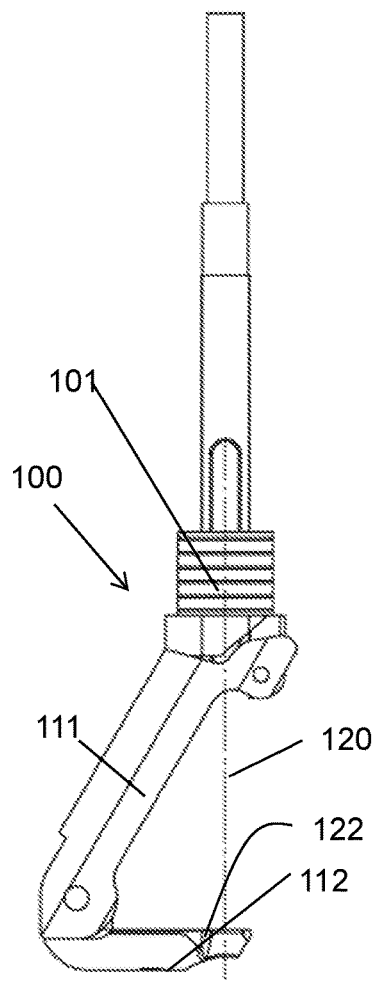
FIGS. 4, 5 and 6 the surgical instrument in a swiveled-out position in two different views and in a longitudinal cross section.
Figure 5:
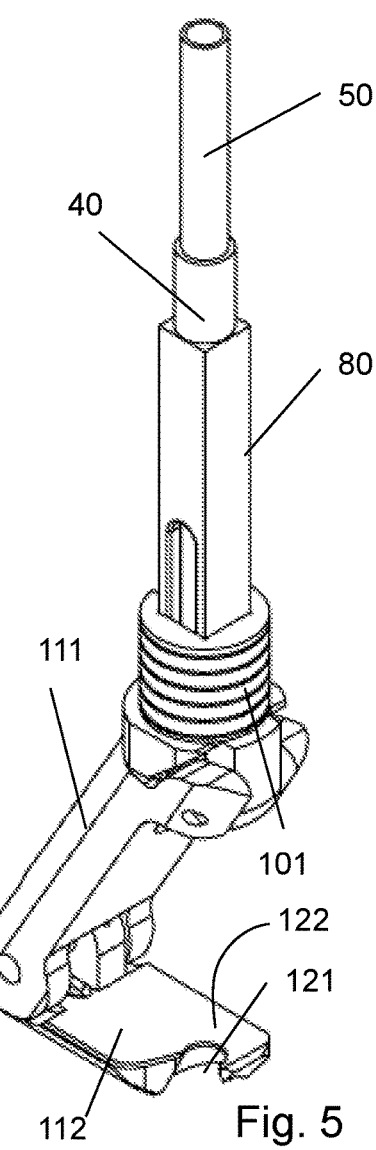
Figure 6:
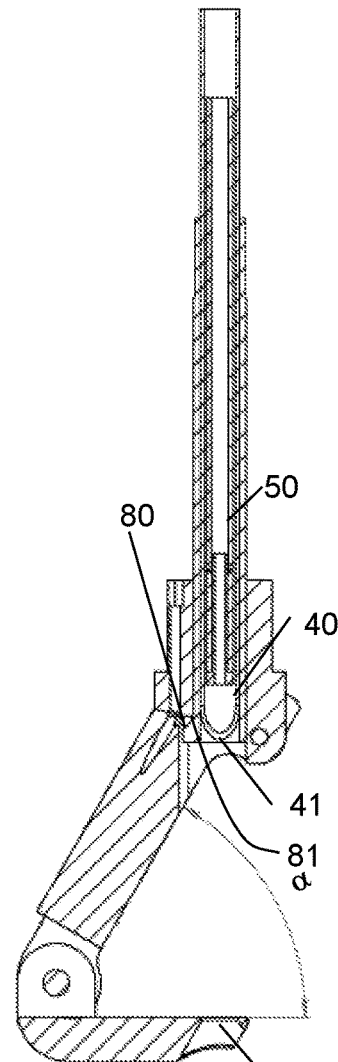

An embodiment of the surgical instrument that implements the leaflet grabbing mechanism is shown in FIGS. 4, 5 and 6. The illustrated mechanism comprises, attached to a further, second tube that is guided inside the first, outer tube, a main body 101, a first arm 111 and a second arm 112 forming a jaw, and a counterportion 80 formed as a pressing member slidable with respect to the main body 101.

Initially, the instrument is in a folded position (see FIGS. 7 and 9 described hereinafter) contained in the outer tube from which the surgeon may release it after it has been advanced into the desired (usually left) atrium. Release may be carried out by retracting the outer tube with respect to the second tube to which the main body is attached.

After release, the arms are caused to swivel out into the position shown in FIGS. 4-6. This may be done by a mechanism that includes an active action by the surgeon, for example as described hereinafter. Alternatively, the device could also be pre-tensioned to swivel out automatically upon release.

In the swiveled-out position, the first arm is at a first angle to the axis 120 that is defined by the first tube and second tube. Especially, the first angle may be not rectangular but acute, for example between 20° and 50°. The second arm 112 is at a second angle $\alpha$ (being 90° minus the first angle) to the first arm, so that the second arm is approximately perpendicular to the axis 120. A proximally facing face 122 of the second arm includes the first abutment surface. A distally facing end face 81 of the counterportion 80 forms the second abutment surface.

Within the counterportion 80 that itself constitutes a distal portion of a third tube, a fourth, inner tube 40 (needle tube) is guided. A distal end of the inner tube 40 is provided with a distal piercing edge 41 to form a needle. Within the inner tube 40, a fifth, anchor carrier tube 50 is present. A distal end of the anchor carrier tube forms an anchor carrier to which the implant is mounted, as for example described in a co-pending application filed by the applicant of the present application on the same day and dealing with a system for repairing an atrioventricular heart valve. Between the carrier tube 50 and the inner tube, a further, intermediate tube (or sleeve) with a non-cutting distal end may be arranged to protect the implant and especially the chord from the edge 41 of the inner tube 40.

The various tubes referred to in this text may, proximally of the described portions, be guided concentrically. Tube materials of plastics, mesh wire, material, such as metal, with appropriate cuts, such as laser cuts, etc. may be used.

Figure 5A:
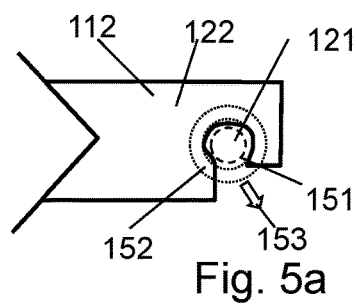
FIG. 5*a*, schematically, a principle implemented by the abutments surface of the second arm.

The second arm 112 with the first abutment surface has a recess 121 that is open to a lateral side. As shown in more detail in FIG. 5a, the shape of the second arm is such that when the second arm is in a released state, inner tube when advanced relative to the main body 101 can go through the recess without encountering the second arm. The dashed circle 151 in FIG. 5a shows the position, in section, of the inner tube when projecting through the first arm. The first abutment surface is formed by that portion of the face 122 against which the distally facing end face 81 is pressable when the counterportion is advanced with respect to the main body 101. In FIG. 5a, the position of this end face, is assumed to be approximately ring shaped and denoted by 152 (dotted line). The first abutment surface will generally be immediately adjacent the recess. In FIG. 5a, the axis 120 runs centrally within the circular area 151 and perpendicularly to the drawing plane.

A ring shape of this distal second abutment surface is not a requirement; rather the abutment surface may have other shapes. Especially, in the depicted embodiments, the counterportion at least towards the depicted distal end has a shape of a slitted tube (with one or two axially running slits) to allow release of the proximal implant part also while the leaflet is being clamped. Thus, the second abutment surface may have a C-shape or the shape of two parallel (I-shape) bars or even an L-shape or a single bar.

The materials of the swivel-out portion may be adapted to the needs of the surgeon. Applicable materials include steel of surgical quality or polymer-based materials such as PEEK. The surface of the arms may be optimized for imaging purposes.

Figure 7:
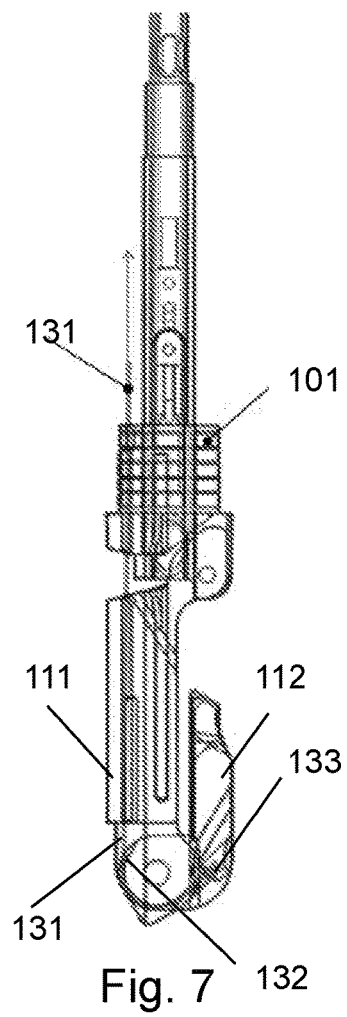
FIGS. 7-9 the swivel-out and swivel-back-in mechanism.
Figure 8:
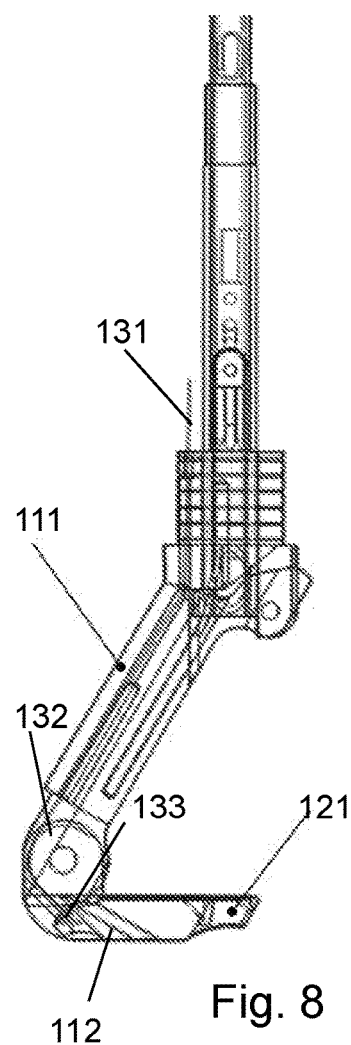
Figure 9:
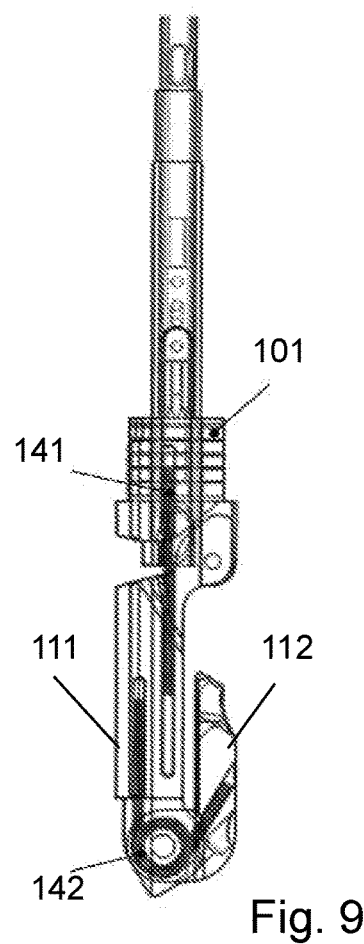

FIG. 7 shows the device in the folded state in which the first arm 111 extends straight (axially) into a distal direction and the second arm, being mounted to the distal end of the first arm, is folded back along the first arm, i.e. lies parallel to the first arm. A steering wire 131 is guided in a small posterior lumen of the main body 101 and the first arm 111, around a guiding structure 132 and leads to an attachment point in the second arm (knot 133.). When the steering wire is pulled, as indicated by the arrow in FIG. 7, the first and second arms 111, 112 are forced into the swiveled-out position (FIG. 8). As shown in FIG. 9, spring elements may be used to pre-tension the device to be in the folded state and thus to spring back into the folded state as soon as the steering wire 131 is released. The spring elements in the depicted embodiment are constituted by a stiffening spring element 141 for orienting the first arm 111 parallel to the axis and a torsion spring 142 for folding the second arm 112 to the first arm 111.

Figure 10:
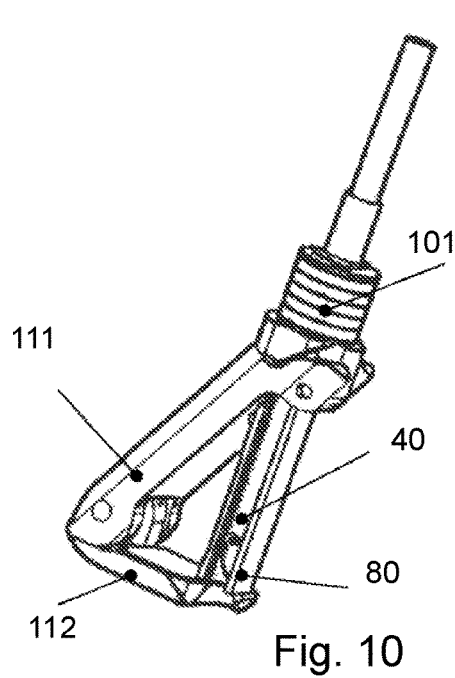
FIGS. 10-15 method steps carried out by the device.
Figure 11:
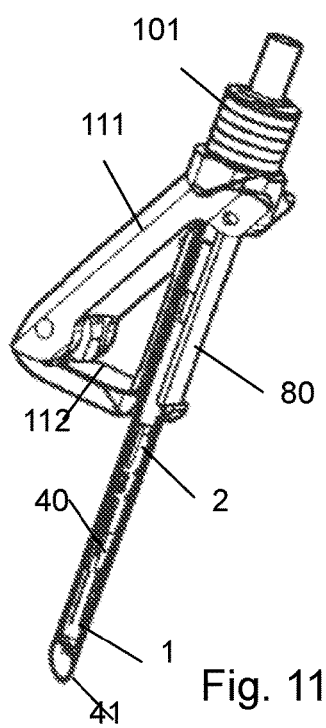
Figure 12:
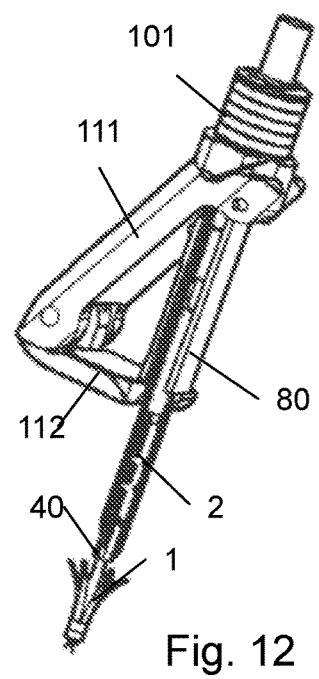

FIGS. 10-15 illustrate the process carried out by the device. FIG. 10 shows the configuration in which the arms 111, 112 are in the swiveled-out position and the counterportion 80 presses against the first abutment surface. This configuration is assumed to clamp an outer portion of the leaflet between the first and second abutment surfaces. Then, as shown in FIG. 11, the inner tube 40 containing the anchor carrier with the proximal implant part 1 and the distal implant part 2 is deployed by being moved towards a distal direction. Thereby it pierces the leaflet and is further advanced until it pierces into tissue, especially muscle tissue, such as the papillary muscle. Then, the inner tube 40 is retracted while the anchor carrier is held still to release the distal implant part 1 that, by the effect of the legs, is anchored in a barb like manner in the tissue (FIG. 12).

An optional sleeve (not shown) of the mentioned kind encompassing the anchor carrier may be used to protect the implant while retracting the inner tube 40 in that the inner tube with the distal piercing edge 41 is retracted first with the sleeve protecting the implant parts, and only thereafter the sleeve is retracted.

Figure 13:
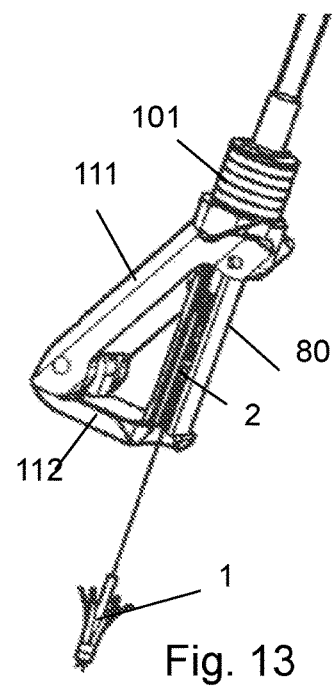

After release of the distal implant part 1, the inner tube 40 is further retracted, together with the anchor carrier holding the proximal implant part 2 (and optionally, if applicable, the sleeve) until the proximal implant part 2 is proximally of the grabbed and clamped leaflet (FIG. 13).

Figure 14:
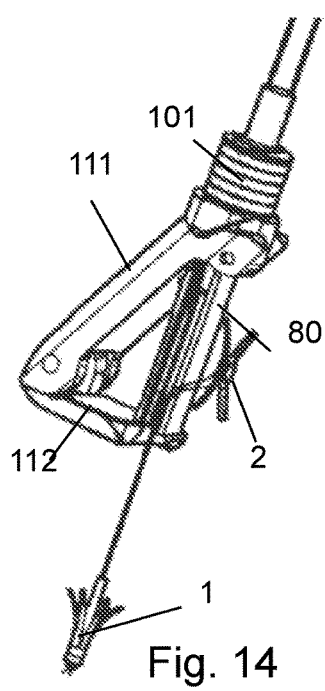

Then, the inner tube is further retracted while the anchor carrier remains in position to release the proximal implant part 2 (FIG. 14). Also this step may optionally include the sub-steps of first retracting the inner tube 40 and only then retracting the sleeve (if applicable) to protect the anchor.

Figure 15:
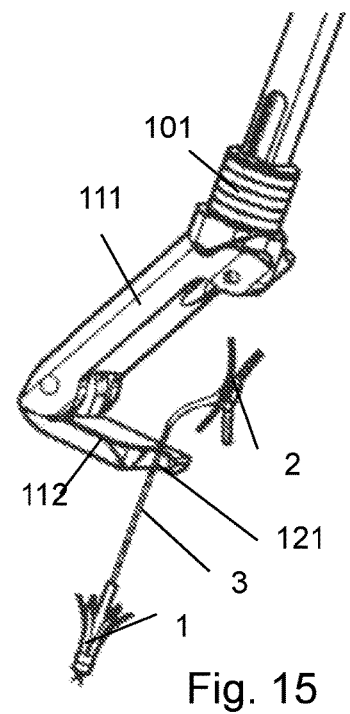

As a result, the implant is set. The leaflet may be released by retracting the counterportion 80 (FIG. 15). The chord may then move relative to the second arm by evading in the direction of the double arrow 153 in FIG. 5a. Thereafter, the arms are folded in into the position shown in FIGS. 7 and 9 and retracted into the outer tube.

What is claimed is:

1. A surgical instrument for repairing an atrioventricular heart valve in a minimally invasive manner, the instrument comprising:
   a first tube having a tube axis defining an axial direction;
   arranged within the first tube, a leaflet grabbing structure, the leaflet grabbing structure comprising a main body, a swivel-out portion with a first arm mounted to the main body, and a second arm, the second arm being swivel-mounted relative to the first arm, the first arm being swivel-mounted with respect to the main body;
   wherein the second arm comprises, in a swiveled-out position of the first and second arms, a proximally facing first abutment surface;
   the leaflet grabbing structure further comprising a counterportion releasable from the tube and being movable a relative to the main body in axial directions, the counterportion comprising a distally-facing second abutment surface that is pressable, by a force pointing towards a distal direction, against the first abutment surface, whereby the leaflet grabbing structure is capable of clamping a leaflet of the heart valve between the first and second abutment surfaces; and
   wherein the second arm has a recess and extends to a position that is central with respect to the tube axis to allow an artificial chord that is released from an interior of the counterportion to extend therethrough while the leaflet is being clamped, and to be released out of the recess by a lateral relative movement
   wherein in a folded position the first arm extends axially distally of the main body, and the second arm is folded back proximally to lie parallel with the first arm.

2. The instrument according to claim 1, wherein the counterportion is straight with respect to the tube axis and is movable in a straight axial direction.

3. The instrument according to claim 1, further comprising a needle arranged in an interior of the counterportion and being movable with respect to the counterportion in axial directions to be released from the interior of the counterportion to pierce the leaflet when it is clamped between the first and second abutment surfaces.

4. The instrument according to claim 3, wherein the needle is cannulated and forms an inner tube, the instrument further comprising an anchor carrier arranged within the inner tube and being axially movable relative to it, the anchor carrier being configured to carry at least a part of an implant that is secured or capable of being secured to the artificial chord.

5. The instrument according to claim 4, wherein the anchor carrier is configured to carry a distal implant part and a proximal implant part of the implant beside one another, with the proximal implant part arranged proximally of the distal implant part.

6. The instrument according to claim 5, wherein the inner tube or a sleeve element inside the inner tube prevents the proximal implant part from escaping from the anchor carrier as long as the anchor carrier is within the inner tube or sleeve element.

7. The instrument according to claim 1, wherein the recess is open to a single lateral side.

8. The instrument according to claim 1, comprising a cable pull mechanism for bringing the first and second arms from the folded position to the swiveled-out position.

9. The instrument according to claim 1, comprising at least one spring element to automatically bring the first arm and/or the second arm into the folded position.

10. The instrument according to claim 9, wherein the spring element or spring elements are capable of bringing both, the first arm and the second arm into the folded position.

11. The instrument according to claim 1, wherein in the swiveled-out position the first arm extends distally from the main body, at an acute angle to the axis.

12. The instrument according to claim 1, wherein the second arm in the swiveled-out position extends essentially perpendicularly to the axis.

13. A method of replacing or supplementing damaged natural chordae tendineae of a human or animal heart of a patient in need thereof, the method comprising the steps of:
provide an instrument according to claim 1
advancing the first tube from an atrial side towards a leaflet of an atrioventricular valve of the heart,
clamping the leaflet between the first and second abutment surfaces;
securing an artificial chord to the clamped leaflet;
removing the leaflet grabbing structure.

14. The method according to claim 13, comprising piercing the leaflet by a needle deployed from the counterportion while the leaflet is being clamped.

15. The method according to claim 13, comprising causing the artificial chord to extend through a perforation of the leaflet while the leaflet is being clamped, and releasing the chord from the leaflet grabbing structure prior to the step of removing by moving it to out of the recess by a lateral relative movement of the chord and the second arm.

16. The method according to claim 13, wherein clamping the leaflet comprises deploying the counterportion until it abuts against the first abutment surface, with the leaflet between the first and second abutment surfaces, and removing the leaflet grabbing structure comprises retreating the counterportion.

* * * * *